United States Patent
Reuter et al.

(10) Patent No.: US 7,667,038 B2
(45) Date of Patent: Feb. 23, 2010

(54) TANTALUM AND NIOBIUM COMPOUNDS

(75) Inventors: Knud Reuter, Krefeld (DE); Daniel Gaess, Marburg (DE); Jörg Sundermeyer, Marburg (DE)

(73) Assignee: H. C. Starck GmbH, Goslar (DE)

( * ) Notice: Subject to any disclaimer, the term of this patent is extended or adjusted under 35 U.S.C. 154(b) by 0 days.

(21) Appl. No.: 12/249,463

(22) Filed: Oct. 10, 2008

(65) Prior Publication Data

US 2009/0099361 A1    Apr. 16, 2009

(30) Foreign Application Priority Data

Oct. 11, 2007    (DE)    ........................ 10 2007 049 015

(51) Int. Cl.
*C07F 9/00*    (2006.01)
*C07D 333/02*    (2006.01)

(52) U.S. Cl. ................................ 546/12; 556/42; 549/3
(58) Field of Classification Search ................... 546/12; 556/42; 549/3
See application file for complete search history.

(56) References Cited

U.S. PATENT DOCUMENTS

| 5,591,483 A | 1/1997 | Winter et al. |
| 6,593,484 B2 | 7/2003 | Yasuhara et al. |
| 2004/0142555 A1 | 7/2004 | Kamepalli et al. |

FOREIGN PATENT DOCUMENTS

WO    WO-00/65123 A1    11/2000

*Primary Examiner*—Charanjit S Aulakh
(74) *Attorney, Agent, or Firm*—Connolly Bove Lodge & Hutz LLP

(57) ABSTRACT

The present invention relates to specific, novel tantalum and niobium compounds which can serve as starting materials for the preparation of chemical vapour deposition (CVD) precursors.

13 Claims, No Drawings

TANTALUM AND NIOBIUM COMPOUNDS

RELATED APPLICATIONS

This application claims benefit of German application 10 2007 049015.3, filed Oct. 11, 2007.

BACKGROUND OF THE INVENTION

Ta— and Ta—N-based mixed system layers for use in Si microelectronics are currently being produced by plasma-based deposition processes (physical vapour deposition, PVD). With regard to the extreme demands for ever more highly integrated circuits, for example conformal layer deposition on structured surfaces, PVD processes are increasingly meeting the limits of practical achievability. For these applications, chemical vapour depositions (CVDs) down to atom layer-specific deposition with a special CVD process, known as atomic layer deposition (ALD), are increasingly being used. For these CVD processes, corresponding chemical starting materials of the individual elements for the particular desired layers must of course be available.

At the present time, for the CVD Ta-based layer structures, predominantly halides are being used, for example $TaCl_5$, $TaBr_5$; see WO 2000065123 A1, A. E. Kaloyeros et al., *J. Electrochem. Soc.* 146 (1999), p. 170-176, or K. Hieber, *Thin Solid Films* 24 (1974), p. 157-164. This is afflicted with various disadvantages. One is that halogen radicals are in many cases undesired for the formation of complex layer structures owing to their etching/corrosive properties, and another is that the tantalum halides have disadvantages as a result of their low volatility and the difficulty of processing them, being high-melting solids. Simple tantalum(V) amides, for example $Ta(N(CH_3)_2)_5$, are likewise proposed; see, for example, Fix et al., *Chem. Mater.*, 5 (1993), p. 614-619. With the simple amides, it is, however, usually possible to establish only particular decomposition ratios of Ta to N, which complicate exact control of the individual element concentrations in the layers. In many cases, Ta—V nitride films form (see, for example, Fix et al.: $Ta_3N_5$) and not the desired electrically conductive Ta(III) nitride layers (TaN). In addition, the films produced with these starting materials very often exhibit high, undesired concentrations of carbon. Tsai et al., *Appl. Phys. Lett.* 67(8), (1995); p. 1128-1130 therefore proposed t-BuN=Ta(NEt$_2$)$_3$ in TaN-CVD at 600° C. Owing to its relatively low volatility, this compound requires a high plant temperature and is therefore not very compatible with the typical production processes of integrated circuits. Other, similar tantalum amide imides have also been proposed; see, for example, Chiu et al., *J. Mat. Sci. Lett.* 11 (1992), p. 96-98, but these produced high carbon contents in the tantalum nitride layers without any further reactive gas. Recently, further tantalum nitride precursors have been proposed, for example by Bleau et al., *Polyhedron* 24(3), (2005), p. 463-468, which, owing to their complexity and complicated preparation, have disadvantages from the outset, or specific cyclopentadienyl compounds which either lead inevitably to TaSiN (not tantalum nitride) or require an additional nitrogen source not specified in detail (Kamepalli et al., US Pat. Appl. Publ. 2004142555 A1, Prior. Jan. 16, 2003, ATMI, Inc.). U.S. Pat. No. 6,593,484 (Kojundo Chemicals Laboratory Co., Ltd., Japan) proposes a suitable specific tantalum amide imide, but the synthesis proposed is difficult and poorly reproducible. R. Fischer et al. describe, in Dalton Trans. 2006, 121-128, mixed hydrazido-amido/imido complexes of tantalum, hafnium and zirconium and their suitability in CVD, but without any statement with regard to the Ta:N ratio in the resulting deposition product. J. Chem. Soc. Dalton Trans. 1990, 1087-1091 describes a trichlorobis(trimethylhydrazido complex), but there is no indication to its use in CVD.

These statements apply essentially or mutatis mutandis also to the analogous niobium compounds and the corresponding CVD chemistry.

BRIEF SUMMARY OF THE INVENTION

There was thus a considerable need for further, novel precursors for TaN and NbN layers. For some applications, there may also be the desire for alternative precursors which are more suitable for the particular application. In this context, it is advantageous to provide starting materials which have a metal-halogen bond, in order to utilize the known reactivity of these compounds toward nucleophilic reagents to prepare the corresponding precursors.

It was thus an object of the present invention to provide novel starting materials for precursors.

The invention relates to tantalum and niobium compounds, especially tantalum compounds, with a divalent hydrazido ligand of the formula (I), which satisfy these requirements. The hydrazido ligands are those of the general formula

where
$R^1$ and $R^2$ are each independently optionally substituted $C_1$- to $C_{12}$-alkyl, $C_5$- to $C_{12}$-cycloalkyl, $C_6$- to $C_{10}$-aryl radicals, 1-alkenyl, 2-alkenyl, 3-alkenyl.

The invention provides compounds of the general formula (II)

where
M is Nb or Ta, preferably Ta,
$R^1$ and $R^2$ are each independently optionally substituted $C_1$- to $C_{12}$-alkyl, $C_5$- to $C_{12}$-cycloalkyl, $C_6$- to $C_{10}$-aryl radicals, 1-alkenyl, 2-alkenyl and 3-alkenyl radicals,
Hal is halogen from the group of F, Cl, Br, I, preferably Cl and Br, more preferably Cl, and
L is an organic complex ligand which coordinates to the metal atom via O, S or N.

DETAILED DESCRIPTION OF THE INVENTION

"Substituted" is understood here, unless mentioned otherwise, to mean substitution by $C_1$- to $C_4$-alkoxy or di($C_1$- to $C_4$-alkyl)amino radicals.

Alkyl is in each case independently a straight-chain, cyclic or branched alkyl radical, where the radicals mentioned may optionally have further substitution.

In the context of the invention, $C_1$-$C_{12}$-alkyl is, for example, methyl, ethyl, n-propyl, isopropyl, 1-ethylpropyl, 1,1-dimethylpropyl, 1,2-dimethylpropyl, 1,3-dimethylpropyl, 1,1,2-trimethylpropyl, 1,2,2-trimethylpropyl, 1-ethyl-1-methylpropyl, 1-ethyl-2-methylpropyl, n-butyl, sec-butyl, tert-butyl, 1-methylbutyl, 2-methylbutyl, 3-methylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, n-pentyl, neopentyl, 1-methylpentyl, 2-methylpentyl, 3-methylpentyl, 4-methylpentyl, n-hexyl, n-heptyl, n-octyl, n-nonyl, n-decyl or n-dodecyl.

1-Alkenyl, 2-alkenyl, 3-alkenyl are, for example, the alkenyl groups corresponding to the above alkyl groups.

$C_5$-$C_{12}$-Cycloalkyl represents, for example, optionally substituted mono-, bi- or tricyclic alkyl radicals. Examples include cyclopentyl, cyclohexyl, cycloheptyl, pinanyl, adamantyl or the isomeric menthyls.

Aryl is in each case independently an aromatic radical having 6 to 10 skeleton carbon atoms, in which no, one, two or three skeleton carbon atoms per cycle may be substituted by heteroatoms selected from the group consisting of nitrogen, sulphur and oxygen, but preferably a carbocyclic aromatic radical having 6 to 10 skeleton carbon atoms.

Examples of optionally substituted $C_6$-$C_{10}$-aryl are phenyl, 2,6-diisopropylphenyl, o-, p-, m-tolyl or naphthyl.

In addition, the carbocyclic aromatic radical or heteroaromatic radical may be substituted by up to five identical or different substituents per cycle which are selected from the group consisting of fluorine, cyano, $C_1$-$C_{12}$-alkyl, $C_1$-$C_{12}$-fluoroalkyl, $C_1$-$C_{12}$-fluoroalkoxy, $C_1$-$C_{12}$-alkoxy or di($C_1$-$C_8$-alkyl)amino.

The ligands L may be identical or different monodentate ligands. They may also together form a bidentate ligand connected via a suitable bridge, for example a $C_2$-$C_6$-alkylene group. Such ligands must not bear any free hydrogen atoms owing to their reactivity with the Hal bonded to the metal atom on the coordinating oxygen, sulphur and nitrogen atoms. Thus, ethers, thioethers or tertiary amines or nitrogen heterocycles are suitable compound classes for the selection of the ligands L.

Suitable monodentate ligands which coordinate via nitrogen are, for example, pyridine, picolines. Suitable bidentate ligands which coordinate via nitrogen are, for example, tetraalkylethylenediamines, such as N,N,N',N'-tetramethylethylenediamine (TMEDA), N,N,N',N'-tetramethyl-1,3-propanediamine, diimines (diazabutadienes) such as N,N'-dialkyl-1,4-diaza-1,3-dienes[N,N'-ethane-1,2-diylidenebisamines] which are N-alkyl-substituted and may bear hydrogen or alkyl groups on carbon atoms 2 and 3, heterocycles such as 2,2'-dipyridyl.

Suitable monodentate ligands which coordinate via oxygen are, for example, ethers (dialkyl ethers such as diethyl ether or methyl tert-butyl ether), cyclic ethers, for example tetrahydrofuran (THF). Suitable bidentate ligands which coordinate via oxygen are, for example, ethylene glycol diethers such as dimethoxyethane (DME), diethoxyethane, longer-chain ethers such as 1,3-dimethoxypropane.

The combination of both means of coordination is also conceivable, for example with bidentate ligands such as 1-dimethylamino-2-methoxyethane.

Suitable monodentate ligands which coordinate via sulphur are, for example, thioethers such as diethyl sulphide or cyclic thioethers such as tetrahydrothiophene.

Here too, the combination of two means of coordination, for example with bidentate ligands containing oxygen and sulphur or nitrogen and sulphur, is possible.

The few examples of hydrazido complexes with end-on structure in the literature—especially the patent application of C. H. Winter et al., U.S. Pat. No. 5,591,483—demonstrate the practical value of specifically this structural feature for CVD.

The examples which follow serve to illustrate the present invention by way of example and should not be interpreted as a restriction.

EXAMPLES

All operations were carried out under protective gas (nitrogen or argon) in apparatus suitable for this purpose (Schlenk technology or gloveboxes).

Example 1

Preparation of Ta(NNMe$_2$)Cl$_3$.2Py 202 mg (0.56 mmol) of tantalum chloride were suspended in 7 ml of toluene and admixed at 60° C. with 0.1 ml of pyridine. After stirring for 10 minutes (min) at 60° C., 115 mg (0.56 mmol) of 1,1-bis(trimethylsilyl)-2,2-dimethylhydrazine=(Me$_3$Si)$_2$NNMe$_2$ were added. After a further 10 min at 60° C., the dark red solution was filtered and the filtrate was blanketed with twice the volume of hexane. After several days, the precipitated dark red crystals were isolated and dried at 0.1 mbar. Yield: 108 mg (0.21 mmol), corresponding to 38% of theory.

$^1$H NMR (C$_6$D$_6$, 200 MHz): δ (ppm)=9.23 (bd, 2H, o-Py); 8.80 (m, 2H, o-Py); 6.81 (bt, 1H, p-Py); 6.64 (m, 1H, p-Py); 6.48 (bt, 2H, m-Py); 6.28 (m, 2H, m-Py); 3.10 (s, 6H, NN(CH$_3$)$_2$).

$^{13}$C NMR (C$_6$D$_6$, 50 MHz): δ (ppm)=152.2; 124.2; 123.9; 47.2 (NN(CH$_3$)$_2$).

Example 2

Preparation of Nb(NNMe$_2$)Cl$_3$.2Py 199 mg (0.74 mmol) of niobium(V) chloride were suspended in 10 ml of toluene and admixed with 154 mg (0.75 mmol) of (Me$_3$Si)$_2$NNMe$_2$. After stirring for 1 hour (h), 2 ml of pyridine were added and the reaction mixture was stirred at 23° C. for a further 16 h. The precipitated brown solid was filtered off and the green filtrate was blanketed with twice the volume of hexane. After several days, the precipitated crystals were isolated and dried at 0.1 mbar. Yield: 94 mg (0.23 mmol), corresponding to 31% of theory.

$^1$H NMR (C$_6$D$_6$, 300 MHz): δ (ppm)=9.29 (bd, 2H, o-Py); 8.79 (m, 2H, o-Py); 6.78 (bt, 1H, p-Py); 6.65 (m, 1H, p-Py); 6.46 (bt, 2H, m-Py); 6.30 (m, 2H, m-Py); 2.93 (s, 6H, NN(CH$_3$)$_2$).

$^{13}$C NMR (C$_6$D$_6$, 75 MHz): δ (ppm)=152.1; 123.9; 123.8; 44.1 (NN(CH$_3$)$_2$).

| Elemental analysis | theoretical: | C 34.7; | H 3.9; | N 13.2 |
|---|---|---|---|---|
| (%, C$_{12}$H$_{16}$N$_4$Cl$_3$Nb) | found: | C 34.8; | H 3.9; | N 13.5 |

Example 3

Preparation of Nb(NNMe$_2$)Cl$_3$.DME 1264 mg (4.68 mol) of niobium(V) chloride were suspended in 50 ml of toluene and admixed with 968 mg (4.74 mmol) of (Me$_3$Si)$_2$NNMe$_2$. After stirring for 1 h, 7 ml of 1,2-dimethoxyethane (DME) were added and the reaction mixture was heated to 90° C. with stirring for 3 h. After cooling to 23° C., the mixture was filtered, and the filtrate was concentrated to half the volume and blanketed with twice the volume of hexane. After 16 h, the precipitated crystals were isolated and dried at 0.1 mbar. Yield: 843 mg (2.43 mmol), corresponding to 52% of theory.

$^1$H NMR (C$_6$D$_6$, 300 MHz: δ (ppm)=3.49 (s, 3H, OCH$_3$); 3.36 (s, 3H, OCH$_3$); 3.06 (m, 4H, OCH$_2$CH$_2$O); 2.74 (s, 6H, N(CH$_3$)$_2$).

$^{13}$C NMR (C$_6$D$_6$, 75 MHz): δ (ppm)=74.3 (OCH$_3$); 67.1 (OCH$_3$); 61.8 (OCH$_2$CH$_2$O); 43.9 (NN(CH$_3$)$_2$).

| Elemental analysis (%, C$_6$H$_{16}$N$_2$O$_2$Cl$_3$Nb) | theoretical: found: | C 20.8; C 20.0; | H 4.7; H 4.6; | N 8.1 N 8.1 |
|---|---|---|---|---|

Example 4

Preparation of Ta(NNMe$_2$)Cl$_3$.TMEDA 2007 mg (5.60 mol) of tantalum chloride were suspended in 150 ml of toluene and admixed at 70° C. with 1162 mg (5.63 mmol) of (Me$_3$Si)$_2$NNMe$_2$. After stirring for 3 h, 1 ml of N,N,N',N'-tetramethylethylenediamine (TMEDA) was added and the reaction mixture was stirred at 70° C. for a further 16 h. After cooling to 23° C., the mixture was filtered and the filtrate was blanketed with twice the volume of n-hexane. After several days, the precipitated violet crystals were isolated and dried at 0.1 mbar. Yield: 1.09 g (2.36 mmol), corresponding to 42% of theory.

$^1$H NMR (C$_6$D$_6$, 300 MHz): δ (ppm)=2.87 (s, 6H, NN(CH$_3$)$_2$); 2.58 (s, 6H, N(CH$_3$)$_2$); 2.47 (2 d, 6H, N(CH$_3$)$_2$); 1.93 (bm, 4H, C$_2$H$_4$).

$^{13}$C NMR (C$_6$D$_6$, 75 MHz): δ (ppm)=59.1; 57.3; 54.6; 50.1; 47.0.

| Elemental analysis (%, C$_8$H$_{22}$N$_4$Cl$_3$Ta) | theoretical: found: | C 20.82; C 20.96; | H 4.82; H 4.80; | N 12.14 N 12.15 |
|---|---|---|---|---|

Example 5 a) Preparation of Li[iPrN)$_2$CNMe$_2$]

1.444 g (28.31 mmol) of LiNMe$_2$ were initially charged in 50 ml of THF and admixed at 0° C. with 3.589 g (28.43 mmol) of diisopropylcarbodiimide. After 10 min, the mixture was warmed to 23° C. and stirred for 1 h. The reaction solution was concentrated to dryness, the evaporation residue was recrystallized from THF and the resulting colourless crystals were dried under reduced pressure. Yield: 4.01 g (22.6 mmol; 80% of theory).

b) Preparation of Li[($^i$PrN)$_2$CCH$_2$SiMe$_3$]

103 mg (1.09 mmol) of LiCH$_2$SiMe$_3$ were initially charged in 10 ml of toluene and admixed with 140 mg (1.10 mmol) of diisopropylcarbodiimide. After stirring at 23° C. for 16 h, the solution was concentrated to dryness and the evaporation residue was recrystallized from THF. The colourless crystals thus obtained were dried under reduced pressure. Yield: 208 mg (0.94 mmol; 86% of theory).

Example 6 a) Preparation of Ta(NNMe$_2$)[($^i$PrN)$_2$CNMe$_2$]$_2$Cl from Ta(NNMe)$_2$Cl$_3$.2Py 200 mg (0.39 mmol) of Ta(NNMe)$_2$Cl$_3$.2Py, prepared according to Example 1, and 141 mg (0.79 mmol) of Li[($^i$PrN)$_2$CNMe$_2$] prepared according to Example 5a) were mixed and admixed at −78° C. with 7 ml of THF at the same temperature. Over 16 h, the mixture was warmed to 23° C. while stirring. The dark orange solution was concentrated to dryness at 20 mbar, taken up in 7 ml of hexane and filtered. The filtrate was concentrated to dryness at 20 mbar and the residue was sublimed at 10$^{-3}$ mbar and 100° C. Yield: 105 mg (0.17 mmol; 44% of theory) as a luminous orange solid; melting point (m.p.). 166° C.

$^1$H NMR (C$_6$D$_6$, 300 MHz, 300 K): δ (ppm)=5.0-3.7 (m, 4H, NCH(CH$_3$)$_2$); 2.89 (s, 6H, NN(CH$_3$)$_2$); 2.7-2.3 (12H, CN(CH$_3$)$_2$); 1.75-1.00 (m, 24 H, NCH(CH$_3$)$_2$).

$^1$H NMR (D$_8$-toluene, 500 MHz, 230 K): δ (ppm)=4.04 (m, 1H, NCH(CH$_3$)$_2$); 3.92 (m, 2H), NCH(CH$_3$)$_2$); 3.79 (m, 1H, NCH(CH$_3$)$_2$); 2.92 (s, 6H, NN(CH$_3$)$_2$); 2.44 (6H, CN(CH$_3$)$_2$); 2.37 (6H, CN(CH$_3$)$_2$); 1.77 (bm, 9H, NCH(CH$_3$)$_2$); 1.69 (d, 3H, NCH(CH$_3$)$_2$); 1.58 (d, 3H, NCH(CH$_3$)$_2$); 1.35 (d, 3H, NCH(CH$_3$)$_2$); 1.27 (d, 3H, NCH(CH$_3$)$_2$); 1.08 (d, 3H, NCH(CH$_3$)$_2$).

$^{13}$C NMR (C$_6$D$_6$, 75 MHz, 300 K): δ (ppm)=48.3 (NN(CH$_3$)$_2$); 47.3 (NCH(CH$_3$)$_2$); 39.8 (CN(CH$_3$)$_2$); 25.1 (NCH(CH$_3$)$_2$). The signal of the quaternary carbon atom of the guanidinato ligand cannot be seen owing to the dynamics of the molecule.

| Elemental analysis (%, C$_{20}$H$_{46}$N$_8$ClTa) | theoretical: found: | C 39.06; C 38.38; | H 7.54; H 7.02; | N 18.22 N 17.61 |
|---|---|---|---|---|

EI-MS: 614 Ta(NNMe$_2$)[($^i$PrN)$_2$CNMe$_2$]$_2$Cl$^+$, 20; 556 Ta[($^i$PrN)$_2$CNMe$_2$]$_2$Cl$^+$, 0.1; 362 Ta($^i$PrN)$_2$CNMe$_2$Cl$^+$, 70; 171 H($^i$PrN)$_2$CNMe$_2^+$, 10; 126 $^i$PrNCN$^i$Pr$^+$, 12; 114 H$_2$CN(CH$_3$)NNN(CH$_3$)CH$_2^+$, 50; 69 $^i$PrNC$^+$, 100; 58 NNMe$_2^+$, 75; 44 NMe$_2^+$, 30.

IR (nujol mull): 1564m, 1518b, 1411m, 1342m, 1325w, 1263m, 1197m, 1141m, 1055s, 1018w, 896m, 800b, 738m, 721m, 597w, 547w.

Example 7

Preparation of Ta(NNMe$_2$)[($^i$PrN)$_2$CCH$_2$SiMe$_3$]$_2$Cl from Ta(NNMe)$_2$Cl$_3$.2Py 702 mg (1.39 mmol) of Ta(NNMe)$_2$Cl$_3$.2Py, prepared according to Example 1, and 622 mg (2.82 mmol) of Li[($^i$PrN)$_2$CCH$_2$SiMe$_3$] prepared according to Example 5b) were mixed in 15 ml of toluene and stirred at 23° C. for 16 h. The solution was concentrated to dryness at 20 mbar and the residue was extracted with 15 ml of hexane. The extract was concentrated to dryness at 20 mbar and the oily residue was distilled at 10$^{-4}$ mbar and 100° C. Yield, 383 mg (0.54 mmol; 39% of theory) as an orange-red, viscous oil.

$^1$H NMR (C$_6$D$_6$, 300 MHz, 300 K): δ (ppm)=3.7-3.5 (bm, 4H, NCH(CH$_3$)$_2$); 2.80 (s, 6H, NN(CH$_3$)$_2$); 1.76 (s, 4H, CH$_2$Si(CH$_3$)$_3$); 1.60-1.20 (bm, 24H, NCH(CH$_3$)$_2$); 0.08 (s, 18H, CH$_2$Si(CH$_3$)$_3$).

$^1$H NMR (D$_8$-toluene, 500 MHz, 260 K): δ (ppm)=3.96 (m, 1H, NCH(CH$_3$)$_2$); 3.82 (m, 1H, NCH(CH$_3$)$_2$); 3.72 (m, 1H, NCH(CH$_3$)$_2$); 3.61 (m, 1H, NCH(CH$_3$)$_2$); 2.87 (s, 6H, NN(CH$_3$)$_2$); 1.74 (s, 2H, CH$_2$Si(CH$_3$)$_3$); 1.72 (d, 3H, NCH(CH$_3$)$_2$); 1.70 (s, 2H, CH$_2$Si(CH$_3$)$_3$); 1.68 (d, 3H, NCH(CH$_3$)$_2$); 1.64 (d, 3H, NCH(CH$_3$)$_2$); 1.60 (d, 3H; NCH(CH$_3$)$_2$); 1.56 (d, 3H, NCH(CH$_3$)$_2$); 1.35 (d, 3H, NCH(CH$_3$)$_2$); 1.26 (d, 3H, NCH(CH$_3$)$_2$); 1.09 (d, 3H, NCH(CH$_3$)$_2$); 0.11 (s, 9H, CH$_2$Si(CH$_3$)$_3$); 0.08 (s, 9H, CH$_2$Si(CH$_3$)$_3$).

$^{13}$C NMR (C$_6$D$_6$, 75 MHz, 300 K): δ (ppm)=48.6 (NN(CH$_3$)$_2$); 25.7-23.3 (NCH(CH$_3$)$_2$); 16.6 (N$_2$CCH$_2$Si(CH$_3$)$_3$); 0.2 (N$_2$CCH$_2$Si(CH$_3$)$_3$). The signal of the quaternary carbon atom of the amidinato ligand cannot be seen owing to the dynamics of the molecule.

| Elemental analysis (%, C$_{24}$H$_{56}$N$_6$ClSi$_2$Ta) | theoretical: found: | C 41.10; C 40.96; | H 8.05; H 7.86; | N 11.98 N 11.88 |
|---|---|---|---|---|

EI-MS: 700 Ta(NNMe$_2$)[($^i$PrN)$_2$CCH$_2$SiMe$_3$]$_2$Cl$^+$, 5; 628 [M-SiMe$_3$]$^+$ 6; 213 ($^i$PrN)$_2$CCH$_2$SiMe$_3$$^+$, 5; 142 H($^i$PrN)$_2$CCH$_3$$^+$, 53; 126 $^i$PrNCN$^i$Pr$^+$, 12; 114 H$_2$CN(CH$_3$)NNN(CH$_3$)CH$_2$$^+$, 50; 73 SiMe3+, 24; 58 NNMe$_2$$^+$, 75; 44 NMe$_2$$^+$, 30.

IR (nujol mull): 1560w, 1552w, 1313wb, 1261m, 1215m, 1178w, 1145m, 1097b, 1018b, 850m, 837m, 798mb, 721s, 597w, 567w, 526w.

Example 8

Preparation of Nb(NNMe$_2$)[($^i$PrN)$_2$CNMe$_2$]$_2$Cl from Nb(NNMe)$_2$Cl$_3$.2Py 300 mg (0.72 mmol) of Nb(NNMe)$_2$Cl$_3$.2Py, prepared according to Example 2, and 258 mg (1.45 mmol) of Li[($^i$PrN)$_2$CNMe$_2$] prepared according to Example 5a) were admixed at 23° C. with 7 ml of THF and stirred for 16 h. In the course of this, the initially green solution turned dark red. The solution was concentrated to dryness at 20 mbar and extracted with 7 ml of hexane, and then the extract was concentrated at 20 mbar down to 1 ml. At −78° C., 175 mg (0.33 mmol; 46% of theory) of the product precipitated out of this as red crystals; m.p. 114° C.

$^1$H NMR (C$_6$D$_6$, 300 MHz, 300 K): δ (ppm)=3.9-3.6 (m, 4H, NCH(CH$_3$)$_2$); 2.82 (s, 6H, NN(CH$_3$)$_2$); 2.46-2.36 (12H, CN(CH$_3$)$_2$); 1.77-1.00 (m, 24H, NCH(CH$_3$)$_2$).

$^{13}$C NMR (C$_6$D$_6$, 75 MHz, 300 K): δ (ppm)=166.8 (CN$_3$); 47.7-45.9 (NN(CH$_3$)$_2$), (NCH(CH$_3$)$_2$); 39.8 (N$_2$CN(CH$_3$)$_2$); 25.4-25.1 (NCH(CH$_3$)$_2$).

| Elemental analysis (%, C$_{20}$H$_{46}$N$_8$ClNb) | theoretical: found: | C 45.85; C 44.39; | H 8.80; H 8.75; | N 21.26 N 21.14 |
|---|---|---|---|---|

EI-MS: 528 M$^+$, 55; 170 ($^i$PrN)$_2$CNMe$_2$$^+$, 55.

IR (nujol mull): 1637s, 1562m, 1518w, 1410m, 1342w, 1315w, 1259s, 1194m, 1097bm, 1057s, 1020bm, 893s, 800bs, 738w, 721m, 605w, 574w, 542w.

Example 9

Preparation of Nb(NNMe$_2$)[($^i$PrN)$_2$CCH$_2$SiMe$_3$]$_2$Cl from Nb(NNMe)$_2$Cl$_3$.2Py 3.66 g (8.80 mmol) of Nb(NNMe)$_2$Cl$_3$.2Py, prepared according to Example 2, and 3.88 g (17.60 mmol, of Li[($^i$PrN)$_2$CCH$_2$SiMe$_3$] prepared according to Example 5a) were admixed at 0° C. with 40 ml of precooled THF and stirred at 0° C. for 20 min. Thereafter, the cooling bath was removed and the mixture was stirred at 23° C. for a further 12 h. The solution was concentrated to dryness at 20 mbar and the residue was extracted twice with a total of 40 ml of hexane. The combined extracts were concentrated to dryness at 20 mbar and the residue was distilled at 10$^{-4}$ mbar and bath temperature 130° C. Yield: 700 mg (1.14 mmol; 13% of theory) as a dark oil.

$^1$H NMR (C$_6$D$_6$, 300 MHz, 300 K): δ (ppm)=3.62 (m, 4H, NCH(CH$_3$)$_2$); 2.80 (s, 6H, NN(CH$_3$)$_2$); 1.76 (s, 4H, CH$_2$Si(CH$_3$)$_3$); 1.55-1.23 (m, 24H, NCH(CH$_3$)$_2$); 0.08 (s, 18H, CH$_2$Si(CH$_3$)$_3$).

$^{13}$C NMR (C$_6$D$_6$, 75 MHz, 300 K): δ (ppm)=49.0 (b, NN(CH$_3$)$_2$); 46.1 (NN(CH$_3$)$_2$); 25.1 (b, NCH(CH$_3$)$_2$); 16.0 (CCH$_2$Si(CH$_3$)$_3$); −0.2 (CCH$_2$Si(CH$_3$)$_3$). The signal of the quaternary carbon atom of the amidinato ligand cannot be seen owing to the dynamics of the molecule.

| Elemental analysis (%, C$_{24}$H$_{56}$N$_6$ClNbSi$_2$) | theoretical: found: | C 47.00; C 46.80; | H 9.20; H 9.12; | N 13.70 N 13.54 |
|---|---|---|---|---|

EI-MS: 612 M$^+$, 55; 213 ($^i$PrN)$_2$CCH$_2$SiMe$_3$$^+$, 55; 156 $^i$PrNCCH$_2$SiMe$_3$$^+$, 85.

IR (nujol mull): 1558m, 1498w, 1342m, 1261m, 1251m, 1209s, 1178m, 1143m, 1124m, 1097m, 1055m, 1018w, 866m, 895w, 850s, 837s, 800bw, 721w, 709w, 646w, 574w, 528w.

The invention claimed is:

1. A compound of the formula (II)

where
M is Nb or Ta,
R$^1$ and R$^2$ are each independently optionally substituted C$_1$- to C$_{12}$-alkyl, C$_5$- to C$_{12}$-cycloalkyl, C$_6$- to C$_{10}$-aryl radicals, 1-alkenyl, 2-alkenyl and 3-alkenyl radicals,
Hal is halogen from the group of F, Cl, Br and I, and
L is an organic complex ligand which coordinates to the metal atom via O, S or N.

2. The compound according to claim 1, wherein Hal is Cl or Br.

3. The compound according to claim 1, wherein Hal is Cl.

4. The compound according to claim 1, wherein L are identical or different monodentate or bidentate ligands.

5. The compound according to claim 3, wherein L are identical or different monodentate or bidentate ligands.

6. The compound according to claim 1, wherein M is Nb.

7. The compound according to claim 1, wherein M is Ta.

8. The compound according to claim 5, wherein M is Nb.

9. The compound according to claim 5, wherein M is Ta.

10. The compound according to claim 1, wherein the ligands L are identical and different and are pyridine, picoline, diimine, ether or tetraalkylethylenediamine.

11. The compound according to claim 1, wherein the ligands L are identical and different and are N,N,N',N'-tetramethylethylenediamine (TMEDA), N,N,N',N'-tetramethyl-1,3-propanediamine, N,N'-dialkyl-1,4-diaza-1,3-diene, 2,2'-dipyridyl, dialkyl ether, cyclic ether, ethylene glycol diether, 1-dimethylamino-2-methoxyethane, thioether or tetrahydrothiophene.

12. The compound according to claim 9, wherein the ligands L are identical and different and are pyridine, picoline, diimine, ether or tetraalkylethylenediamine.

13. The compound according to claim 9, wherein the ligands L are identical and different and are N,N,N',N'-tetramethylethylenediamine (TMEDA), N,N,N',N'-tetramethyl-1,3-propanediamine, N,N'-dialkyl-1,4-diaza-1,3-diene, 2,2'-dipyridyl, dialkyl ether, cyclic ether, ethylene glycol diether, 1-dimethylamino-2-methoxyethane, thioether or tetrahydrothiophene.

* * * * *